United States Patent [19]

Broughton et al.

[11] Patent Number: 4,550,736
[45] Date of Patent: Nov. 5, 1985

[54] MOVEMENT ARTIFACT DETECTOR FOR SLEEP ANALYSIS

[75] Inventors: Roger Broughton; Bernardo da Costa, both of Ottawa, Canada

[73] Assignee: Canadian Patents & Development Limited, Ottawa, Canada

[21] Appl. No.: 659,295

[22] Filed: Oct. 10, 1984

[30] Foreign Application Priority Data

Oct. 14, 1983 [CA] Canada .................................. 439061

[51] Int. Cl.4 ............................................. A61B 5/04
[52] U.S. Cl. .................................................. 128/731
[58] Field of Search ......................................... 128/731

[56] References Cited

U.S. PATENT DOCUMENTS 4,417,592  11/1983  John ..................................... 128/731

Primary Examiner—Kyle L. Howell
Assistant Examiner—Francis J. Jaworski
Attorney, Agent, or Firm—Edward Rymek

[57] ABSTRACT

The movement detector monitors the electroencephalogram (EEG) signal in order to detect components having a real-time frequency greater than 30 Hz and an amplitude greater than 18 $\mu$V; a real-time frequency greater than 30 Hz and an amplitude between $\pm 9$ $\mu$V; or a real-time frequency less than 1.2 Hz and an amplitude greater than 200 $\mu$V. An output signal is provided when at least one of these components is detected.

5 Claims, 2 Drawing Figures

MOVEMENT ARTIFACT DETECTOR FOR SLEEP ANALYSIS

BACKGROUND OF THE INVENTION

This invention is directed to automatic sleep analysers and, in particular, to detectors for the specific events used in staging sleep.

A scoring system for staging the sleep patterns of adult humans has been standardized and is described in the manual edited by A. Rechtschaffen and A. Kales entitled, "A Manual of Standardized Terminology, Techniques and Scoring System for Sleep Stages of Human Subjects", Public Health Service, U.S. Government Printing Office, Washington D.C., NIH Publ. No. 204, 1968.

In scoring sleep, three basic signals recorded as electrical activity in the body, are required. These are the activity of the brain, the eyes and the muscles. The activity of the brain is represented by an electroencephalographic (EEG) signal obtained from electrodes placed on the head. The activity of the eyes is represented by electro-oculo-graphic (EOG) signals obtained from electrodes placed near each eye. The muscle tone activity is represented by an electromyographic (EMG) signal obtained from electrodes usually located under the chin.

The activity signals would normally be recorded on a paper printout, and divided into time segments or epochs, e.g. of forty seconds. Specific events are noted visually during each epoch in order to classify that epoch as a certain state of sleep or non-sleep. The conventional seven states of sleep or non-sleep are known as wakefulness, stage 1 sleep, stage 2 sleep, stage 3 sleep, stage 4 sleep, REM sleep and movement time. These are listed in Table 1 together with the criteria for each epoch state used in the classification. The events used to stage or classify these states are alpha rhythm, sleep spindles, delta activity, and movement artifact which are observed in the EEG signals, rapid eye movements (REM) which is observed in the EOG signal, and muscle tone which is observed in the EMG signal.

TABLE 1

| | Criteria for Sleep Staging | | | | | | |
|---|---|---|---|---|---|---|---|
| | | | State | | | | |
| Event | W | 1 | 2 | 3 | 4 | REM | M.T. |
| Alpha | ± | 0 | 0 | 0 | 0 | ± | ± |
| Spindles | 0 | 0 | + | ± | ± | 0 | ± |
| Delta | 0 | 0 | <20% | 20-50% | 50-100% | 0 | ± |
| Mov't artifact | ± | 0 | 0 | 0 | 0 | 0 | >50% |
| REM | ± | 0 | 0 | 0 | 0 | + | ± |
| EMG | + | ± | ± | ± | ± | 0 | + |

Table 1 lists the events and their levels which are to be observed during an epoch in order to classify it into a particular state. However, in addition to this table, certain guidelines exist for staging sleep by which the state in each epoch can only be determined by observing events that occur in previous or subsequent epochs.

Traditional sleep recording with a monitoring technologist is very time consuming and expensive, involving overnight shift work and slow visual analyis of very long paper recordings. The need for a monitoring technologist can be avoided and, in many cases, be replaced by using portable recordings placed on the subject to record the required signals continuously in his normal home environment. The slow visual analysis of long paper recordings can be circumvented by the use of automatic analysis, at high speed playback, of tape recorded data from either portable or traditional in-laboratory recordings. Automatic analysis can replace such long recordings by summary statistics and charts, and also improve scoring consistency.

A number of centers have attempted various approaches to automatic sleep analysis as a particular extension of the problem of automatic EEG analysis. Sleep EEG events have most frequently been detected by spectral analysis, by pattern recognition, and by period analysis of zero-crossing data. As well, digital filters have recently been introduced and have potential application in the field. Combinations of these methods have sometimes been used to detect individual sleep EEG events which combine zero-crossing analysis with an amplitude criterion, a period discriminator to determine frequency band (delta, alpha, spindle, beta or muscle potential), plus a pattern criterion. The staging of sleep may be done using detectors based on the above approaches which are then combined in a "hard wired" processing unit. Alternately, all data processing for sleep staging may be done by a large general purpose computer. The hard-wired sleep stagers have the advantage of lower cost, but the great disadvantage of being inflexible. Performing all analyses on digitalized raw data in a necessarily large general purpose computer, on the other hand, is very expensive.

An intermediate approach, in which the present invention is used, has a series of (sometimes modifiable) event detectors as part of a preprocessor unit. The detectors detect essentially only those events which are used for visual analysis. Their outputs can then be analysed for quantification of sleep variables and for sleep staging, either visually, or automatically by a microprocessor or a small general purpose computer. Gaillard and Tissot have chosen a somewhat similar approach, as described in their publication, "Principles of automatic anaylsis of sleep records with a hybrid system", Comp. Biomed. Res., 1973, 6:1-13. In this system the outputs of a preprocessor consisting of 12 bandpass filters for EEG analysis, an eye movement analyser, a muscle integrator, an EKG counter, and a galvanic skin response (GSR) counter are coupled to a small general purpose computer. Such an approach combines the advantages of relatively low cost and flexibility.

As described above, the events to be detected are alpha rhythm, sleep spindle, delta activity, and movement artifact in the EEG signal, plus REMs and muscle tone.

The alpha rhythm in automatic sleep analysers is generally detected using a classical bandpass filter or zero-crossing detector and a level discriminator. A particularly useful phase-locked loop alpha detector is described in the thesis entitled, "A Hybrid Pre-Processor for Sleep Staging Using the EEG", by D. Green, 1977, Chapter 7, pp. 1 to 13. This detector produces an output, when the EEG signal has a component with a frequency of 8-12 Hz at greater than 25 $\mu$V peak-to-peak amplitude.

The sleep spindle is the sleep EEG event most comprehensively examined to date. The approaches to spindle detection include: zero-crossing methods, classical analogue bandpass filtering, bandpass filtering with harmonic analysis, a software Fast Fourier Transform (FFT) approach, a matched filter approach, and a phase-locked loop (PLL) approach. A highly accurate sleep spindle detector is described in the publication by R. Broughton et al, entitled "A Phase-locked Loop Device for Automatic Detection of Sleep Spindles and Stage 2", Electroencephalography and Clinical Neurophysiology, 1978, 44: 677–680. This detector produces an output when the EEG signal has a component with a frequency of 11.5–15 Hz at greater than 14 $\mu$V peak-to-peak and a minimum burst duration of 0.5 seconds.

Delta activity detection can be performed by using analogue bandpass filters with energy detectors, by zero-crossing analysis using amplitude and period criteria, or by a software approach. A particularly useful delta detector which detects components of the EEG signal having a frequency of 0.5–1.5 Hz at greater than 67 $\mu$V peak-to-peak, is described in the above noted thesis, chapter 9, pp. 1 to 10.

Of the three remaining event detectors required for sleep analysis, a Muscle Tone Detector and an Eye Movement Detector are described in co-pending U.S. patent application Ser. Nos. 659,296 and 659,297 filed on even date herewith by R. Broughton et al.

SUMMARY OF THE INVENTION

It is therefore an object of the present invention of provide a movement detector for a sleep analyser.

This and other objects are achieved in a detector which receives an electroencephalogram (EEG) signal that is to be monitored for three specific ranges of signal components. The first monitor detects components in the EEG signal having a real-time frequency greater than approximately 30 Hz and an amplitude greater than 18 $\mu$V. The second monitor detects components in the EEG signal having a real-time frequency greater than approximately 30 Hz and an amplitude between approximately $\pm 9$ $\mu$V. The third monitor detects components in the EEG signal having a real-time frequency less than approximately 1.2 Hz and an amplitude greater than approximately 200 $\mu$V. The three monitors are connected to provide an output when at least one of the three component ranges are present. This may be done through an OR-gate connected to each of the monitors.

Many other objects and aspects of the invention will be clear from the detailed description of the drawings.

DETAILED DESCRIPTION

Figure 1:
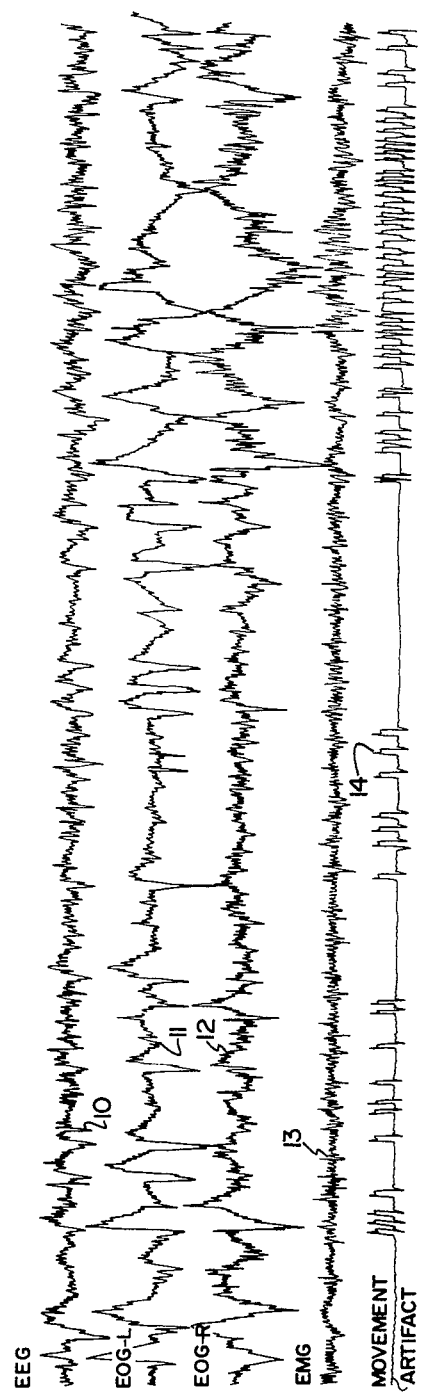
FIG. 1 illustrates examples of the EEG, EOG, and EMG signals used in sleep analysis and the output of the movement artifact detector.

The movement artifact detector operates on the electroencephalogram (EEG) signal obtained from electrodes placed on the head. The signals are usuallly preamplified and recorded in real time on one channel of an EEG apparatus or a magnetic tape recorder. An example of an EEG signal 10 is illustrated in FIG. 1 together with signals on the other channels, i.e. the left and right EOG signals 11 and 12, and the electromyogram signal 13.

The movement artifact detector, in accordance with the present invention, operates on the EEG signal. In order to save analysis time, the EEG signals may be fed to the detector at a much greater speed than that at which they were recorded. The detector will be described in terms of real-time parameters, the actual parameters of the detector will, of course, depend on the actual speed at which it is designed to operate. The movement artifact detector does not detect one specific event, but monitors the EEG signal to determine 5 to 30 second periods of each epoque, which are uninterpretable, i.e. do not clearly exhibit sleep events. In order to achieve this consistently, in accordance with the Rechtschaffen and Kales standard, the EEG signal is monitored to detect:

(1) A high frequency EMG signal over-riding the EEG signal;
(2) Iso-electric signals characterizing amplifier blocking, and slow recovery to normal EEG levels; and
(3) Very high amplitude, low frequency signals. Typically, these are of higher amplitude and lower frequency than EEG delta activity and are due to breathing, sweating, electrode wire or other artifacts.

Figure 2:
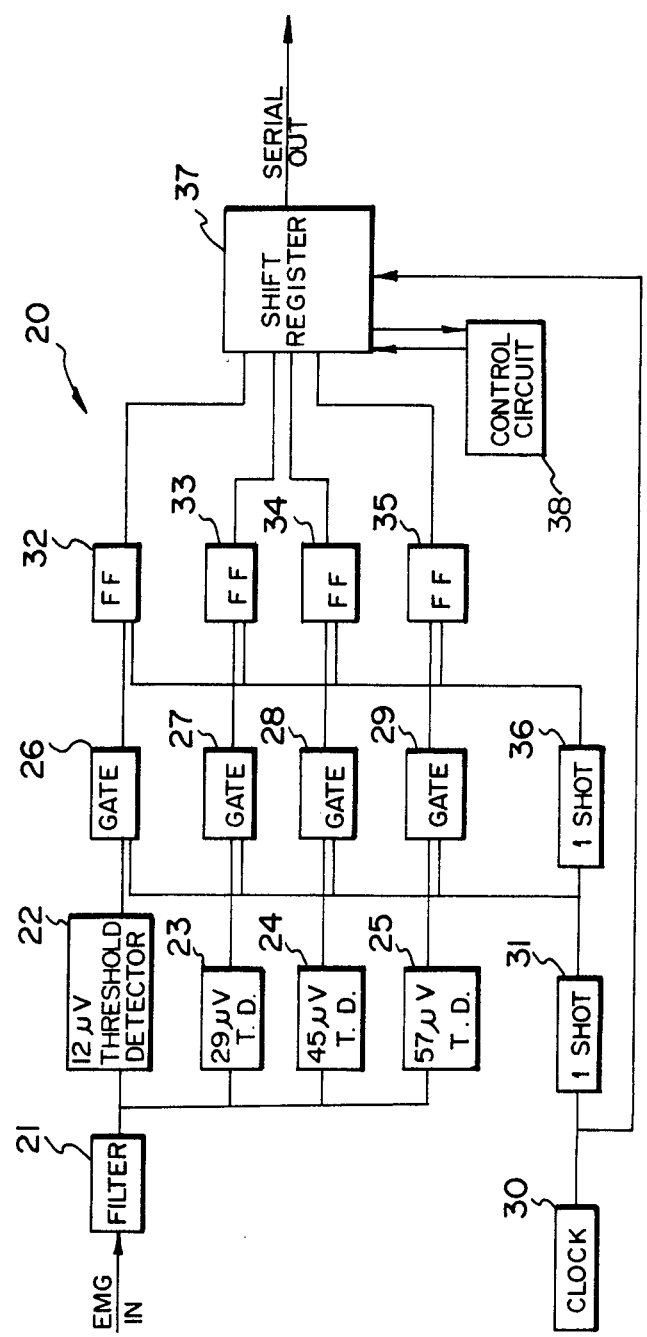
FIG. 2 illustrates a movement detector in accordance with the present invention.
Figure 2:
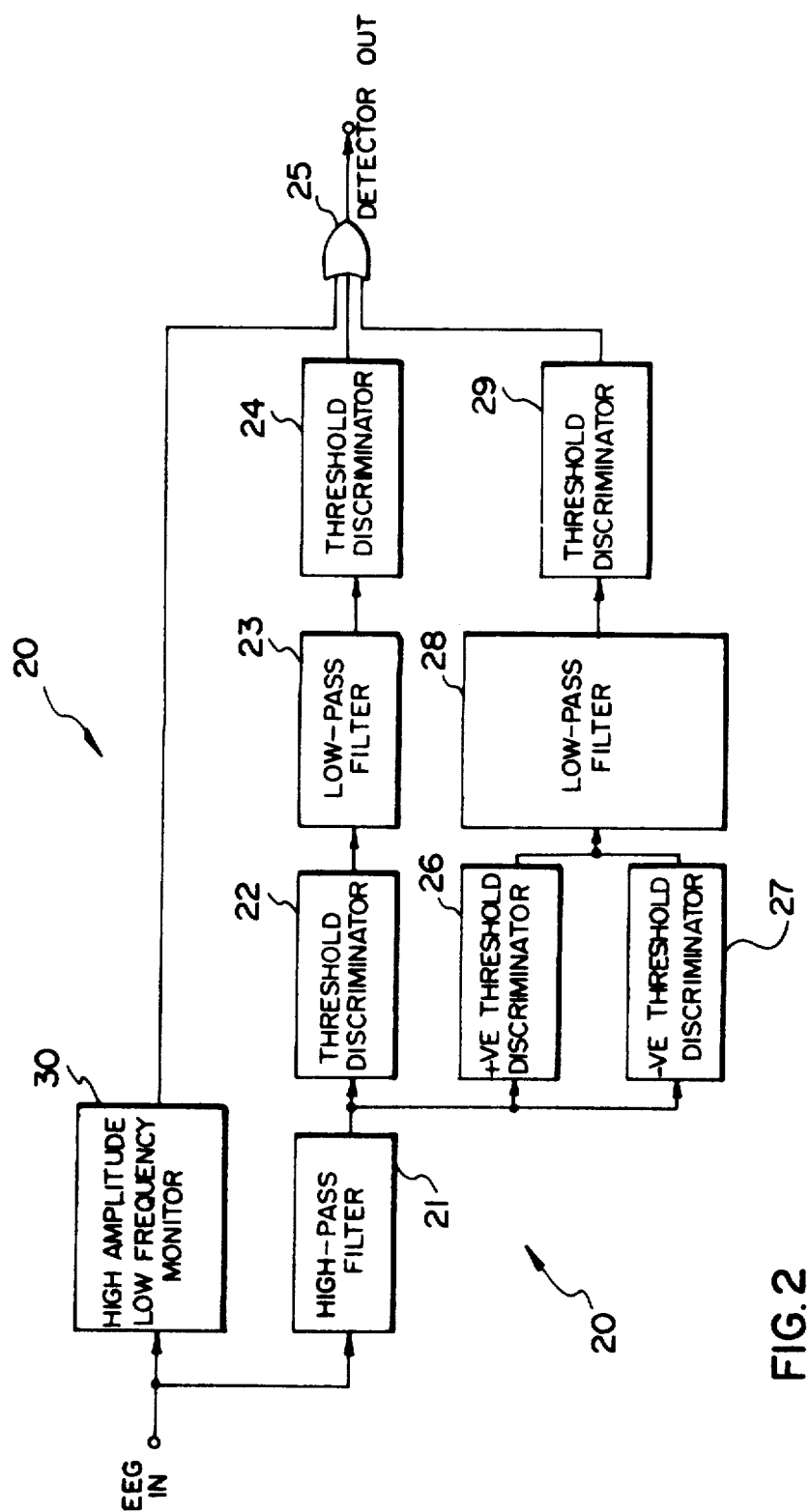

A movement artifact detector is illustrated in FIG. 2. To detect the signals as set out in 1 and 2 above, the detector 20 includes a high-pass filter 21 set to filter out all components having a real-time frequency below 30 Hz. The filtered signal is applied to three threshold discriminators 22, 26 and 27. The voltage level of discriminator 22 is set at +18 V and thus all high amplitude components are passed to provide a positive output which is fed to a low-pass filter that may be a simple RC circuit wherein the output voltage is averaged across the capacitor. This low frequency signal is applied to a further threshold discriminator 24 which produces a logical one or zero depending on the amplitude of the signal applied to it. The threshold discriminator 24 is connected to one of three inputs of an OR-gate 25 which produces a logical 1 if any one of its inputs are high. This circuit thus detects the high over-riding EMG signal which appears on the EEG signal.

To detect the iso-electric signal which appears on the EEG signal, a positive threshold discriminator 26 and a negative threshold discriminator 27 are connected in parallel to the output of highpass filter 21. These discriminators are set at +9 $\mu$V and $-9$ $\mu$V, respectively, with their outputs wired together such that an output is provided only when the high frequency signal falls between +9 $\mu$V and $-9$ $\mu$V. This output is again passed through a low pass filter 28 and a further threshold discriminator 29 provides a logic 1 or 0 depending on the amplitude of the input signal to it. The output of discriminator 29 is connected to a second input of OR-gate 25.

The third monitor 30 in the movement detector 20 is used to detect components in the EEG signal that have a real-time frequency of less than 1.2 Hz but with an amplitude greater than 200 $\mu$V. Monitor 30 may simply include a low pass filter and a threshold discriminator. Alternately, it may consist of a delta detector of the type described in the above noted thesis by Green, Chapter 9, pp. 1 to 10, however, with the component and settings modified to detect all frequencies below 1.2 Hz and only amplitudes above 200 $\mu$V. The output of monitor 30 is connected to the third input of OR-gate 25.

Thus, if any of the three types of signal discussed above are present on the EEG signal, OR-gate 25 will provide an output. Such an output signal 14 is shown in FIG. 1. This output signal is then used to stage the epoques in which it appears.

Many modifications in the above described embodiments of the invention can be carried out without departing from the scope thereof and, therefore, the scope of the present invention is intended to be limited only by the appended claims.

We claim:

1. A movement detector for a sleep analyser comprising:

means for receiving an electroencephalogram (EEG) signal;

first monitoring means for detecting only components in the EEG signal having a real-time frequency greater than approximately 30 Hz and greater than a first predetermined amplitude;

a second monitoring means for detecting only components in the EEG signal having a real-time frequency greater than approximately 30 Hz and a second predetermined amplitude smaller than the first predetermined amplitude;

third monitoring means for detecting only components in the EEG signal having a real-time frequency less than approximately 1.2 Hz and a third predetermined amplitude at least an order in magnitude greater than the first predetermined amplitude; and means connected to the first, second and third monitoring means for providing an output only if at least one of the predetermined components are detected.

2. A movement detector as claimed in claim 1 wherein the first predetermined amplitude is approximately 18 $\mu V$, the second predetermined amplitude is between approximately $\pm 9$ $\mu V$, and the third predetermined amplitude is approximately 200 $\mu V$.

3. A movement detector as claimed in claim 2 wherein the first monitoring means includes a high-pass filter, a first threshold discriminator connected to the high-pass filter, a first low-pass filter connected to the first discriminator and a second threshold discriminator connected to the first low-pass filter to provide an output when predetermined components are present in the EEG signal.

4. A movement detector as claimed in claim 3 wherein the second monitoring means includes a positive threshold discriminator and a negative threshold discriminator connected in parallel to the high-pass filter, a second low-pass filter for receiving the combined outputs of the negative and positive threshold discriminators and a threshold detector connected to the second low pass filter to provide an output when predetermined components are present in the EEG signal.

5. A movement detector as claimed in claim 4 wherein the output means includes an OR-gate.

* * * * *

UNITED STATES PATENT AND TRADEMARK OFFICE
CERTIFICATE OF CORRECTION

PATENT NO. : 4,550,736

DATED : November 5, 1985

INVENTOR(S) : Roger Broughton - Bernardo da Costa

It is certified that error appears in the above-identified patent and that said Letters Patent are hereby corrected as shown below:

Figure 2 is replaced by the attached Figure 2.

*Signed and Sealed this*

*Eighteenth* Day of *March 1986*

[SEAL]

Attest:

DONALD J. QUIGG

*Attesting Officer*

*Commissioner of Patents and Trademarks*